United States Patent [19]

Jones

[11] Patent Number: 5,638,949

[45] Date of Patent: Jun. 17, 1997

[54] PACKAGED CONDOM

[75] Inventor: Keith Graham Jones, Monaco Ville, Monaco

[73] Assignee: Motech Sam, Monaco

[21] Appl. No.: 648,691

[22] Filed: May 16, 1996

[51] Int. Cl.⁶ .................................................. B65D 85/14
[52] U.S. Cl. ................................. 206/69; 206/37
[58] Field of Search ................... 206/69, 438, 37, 206/493

[56] References Cited

U.S. PATENT DOCUMENTS

| | | | |
|---|---|---|---|
| 5,316,019 | 5/1994 | Jones | 206/69 X |
| 5,316,136 | 5/1994 | Castagna | 206/69 |
| 5,437,286 | 8/1995 | Stratton | 206/69 X |

*Primary Examiner*—Jacob K. Ackun
*Attorney, Agent, or Firm*—Iandiorio & Teska

[57] ABSTRACT

A packaged condom (2) comprising a first container (4), a second container (6) positioned inside the first container (4), and a condom (8) sealed inside the second container (6): the first container (4) comprising a base (10) and an upstanding side wall (12); the second container (6) comprising a base (14), an upstanding side wall (16), and an upstanding locating member (18); and the packaged condom (2) being such that the first and the second containers (4, 6) are separable from each other such that after use of the condom (8) the first and the second containers (4, 6) are connectable together to form a closed receptacle for the used condom (8).

10 Claims, 3 Drawing Sheets

PACKAGED CONDOM

This invention relates to a packaged condom.

Condoms are traditionally packaged by being individually sealed in metallised film. The sealed condoms are then sold in packets containing predetermined numbers of the sealed condoms. The metallised film is flexible and can be damaged. Also, the metallised film gives no indication of which way up the condom is inside the metallised film. Still further, the metallised film provides no assistance whatsoever in disposing of the condom after use.

It is an aim of the present invention to obviate or reduce the above mentioned problems.

Accordingly, in one non-limiting embodiment of the present invention there is provided a packaged condom comprising a first container, a second container positioned inside the first container, and a condom sealed inside the second container: the first container comprising a base and an upstanding side wall; the second container comprising a base, an upstanding side wall, and an upstanding locating member; the condom comprising a closed end portion which is located on the upstanding locating member; and the packaged condom being such that the first and the second containers are separable from each other such that after use of the condom the first and the second containers are connectable together to form a closed receptacle for the used condom.

The packaged condom of the present invention is thus such that initially the condom is able to be hermetically sealed inside the second container. By virtue of the fact that the first and the second containers each have a base and an upstanding side wall, the first and the second containers can be made to be rigid which protects the condom prior to use. The location of the closed end of the condom on the upstanding locating member means that when the packaged condom is opened, the condom will always be the right way up. A person only has to feel for the upstanding locating member to know that the condom is the right way up. Thus the packaged condom of the present invention facilitates easy use, even in the dark. After use, the ability of the first and the second containers to be connected together to form a closed receptacle for the used condom provides a convenient, discreet and hygienic method of storing the used condom for disposal.

Preferably, the packaged condom is one in which the first and the second containers are connectable together to form a closed receptacle which is not re-openable.

Preferably, the packaged condom is one in which the first and the second containers are connectable together to form the closed receptacle such that the second container forms a lid for the first container. The second container is preferably such that it is turned upside down to form the lid for the first container.

The packaged condom may be one in which the side wall of the first container has an inner face with a peripheral groove in it, in which the side wall of the second container has an outwardly directed lip, and in which the lip locates in the peripheral groove when the first and the second containers are connected together to form the closed receptacle. The peripheral groove may have an upper edge defined by a peripheral bead which acts to lock the first and the second containers together when they are connected together to form the closed receptacle.

Preferably, the second container has a foil seal for sealing the condom in the second container. The foil seal will usually be a metallised plastics laminate foil seal. The metallised plastics laminate is preferably an aluminium plastics laminate.

The foil seal may have a pull portion for enabling the foil seal to be opened.

Preferably, the foil seal extends over the first container and thus seals the second container in the first container.

The foil seal may be heat sealed in position. Other means of securing the foil seal in position may be employed.

Preferably, the closed end portion of the condom is in the form of a teat. If desired, the closed end of the condom can be simply curved and not in the form of a teat.

The packaged condom may include an applicator for applying the condom. The applicator may be used to enable persons to avoid or minimise hand contact with the condom.

Preferably, the applicator is in the form of a ring which has a grooved portion for holding the condom. The ring may have a frangible joint which is adapted to be broken during use of the ring in applying the condom, thereby enabling the ring to be removed from the base of a penis after it has been used to unroll the condom along the length of the penis.

An embodiment of the invention will now be described solely by way of example and with reference to the accompanying drawings in which.

Figure 1:
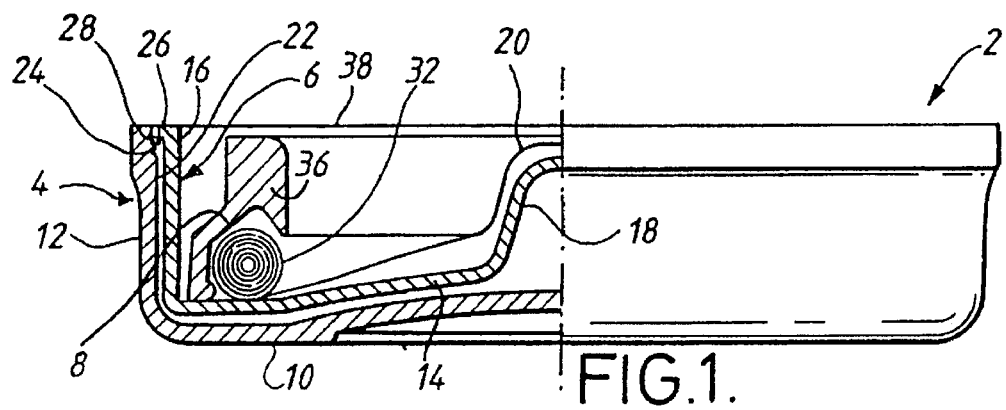
FIG. 1 is a side view, partially in section, of a packaged condom of the invention.

Referring to the drawings, there is shown a packaged condom 2 comprising a first container 4 and a second container 6 positioned inside the first container 4. A condom 8 in a rolled form as shown in FIG. 1 is sealed inside the second container 6.

The first container 4 comprises a base 10 and an upstanding side wall 12. The second container 6 comprises a base 14 and an upstanding side wall 16. The first and the second containers 4, 6 are circular in plan as can be appreciated from FIG. 5 and they are in the form of shallow dishes.

The second container 6 has an upstanding locating member 18. The condom 8 has a closed end portion 20 and this closed end portion 20 is located on the upstanding locating member 18.

Figure 2:
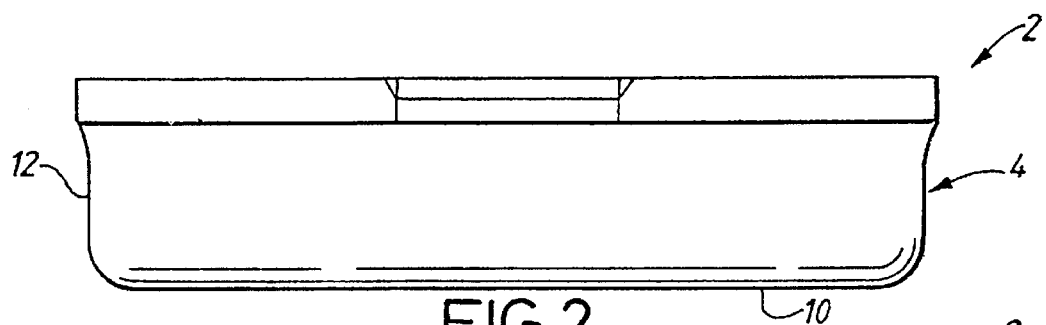
FIG. 2 is a side view of the packaged condom as shown in FIG. 1.
Figure 3:
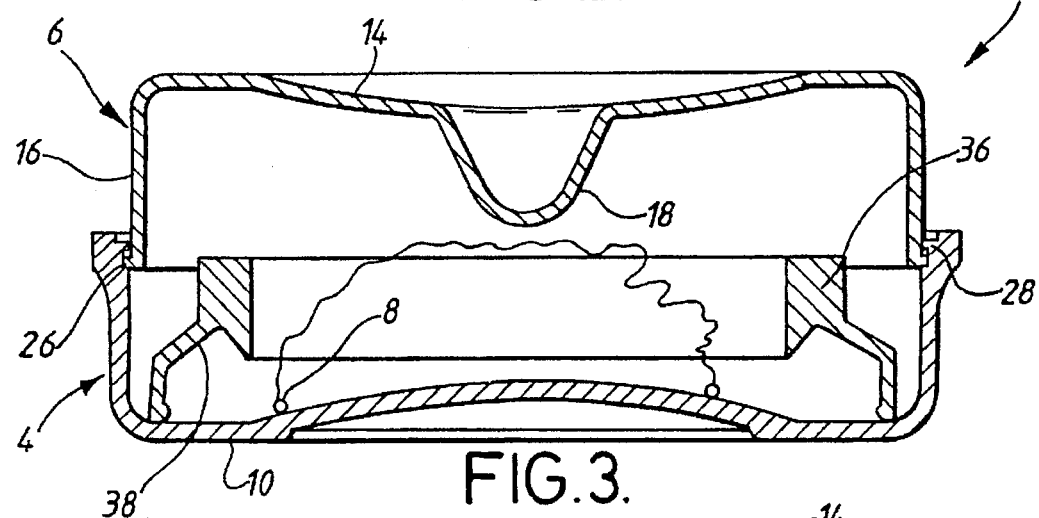
FIG. 3 is a sectional side view of the packaged condom shown in FIG. 1 but with first and second containers forming part of the packaged condom being connected together to form a closed receptacle for a used condom.
Figure 4:
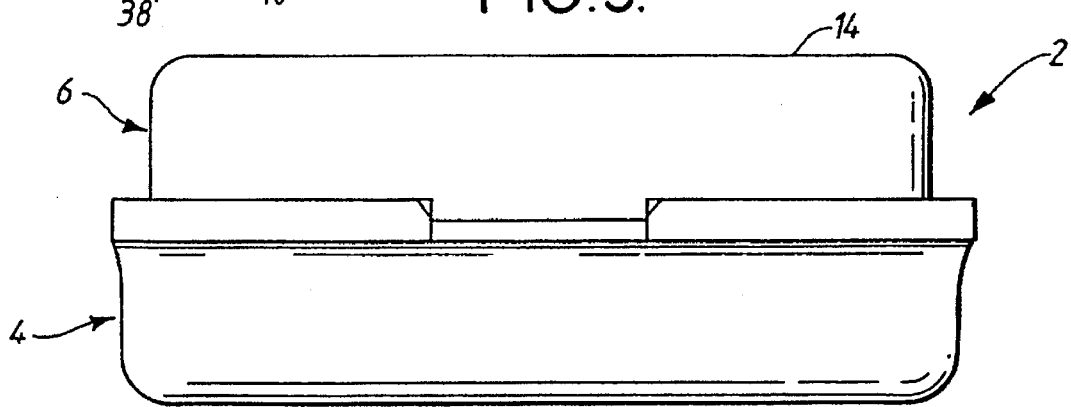
FIG. 4 is a side view of the packaged condom as shown in FIG. 3.

The packaged condom 2 is such that the first and the second containers 4, 6 are separable from each other such that after use of the condom 8, the first and the second containers 4, 6 are connectable together to form a closed receptacle for the used condom 8. FIGS. 1 and 2 show the position of the first and the second containers 4, 6 prior to use of the condom. FIGS. 3 and 4 show the position of the first and the second containers 4, 6 after use of the condom.

In FIGS. 3 and 4, the first and the second containers 4, 6 are connected together to form a closed receptacle which is not re-openable. As can also be seen from FIGS. 3 and 4, the first and the second containers 4, 6 are connected together to form the closed receptacle such that the second container 6 forms a lid for the first container 4. This is effected by turning the second container 6 upside down, that is the second container 6 in the position shown in FIG. 1 is turned upside down in order to achieve its position shown in FIG. 3.

The side wall 12 of the first container 4 has an inner face 22 with a peripheral groove 24 in it. The side wall 16 of the second container 6 has an outwardly directed lip 26. The lip 26 locates in the peripheral groove 24 when the first and the second containers 4, 6 are connected together to form the closed receptacle as shown in FIGS. 3 and 4. The peripheral groove 24 has an upper edge defined by a peripheral bead 28. The peripheral bead 28 acts to lock the first and the second containers 4, 6 together when they are connected together to form the closed receptacle.

Figure 5:
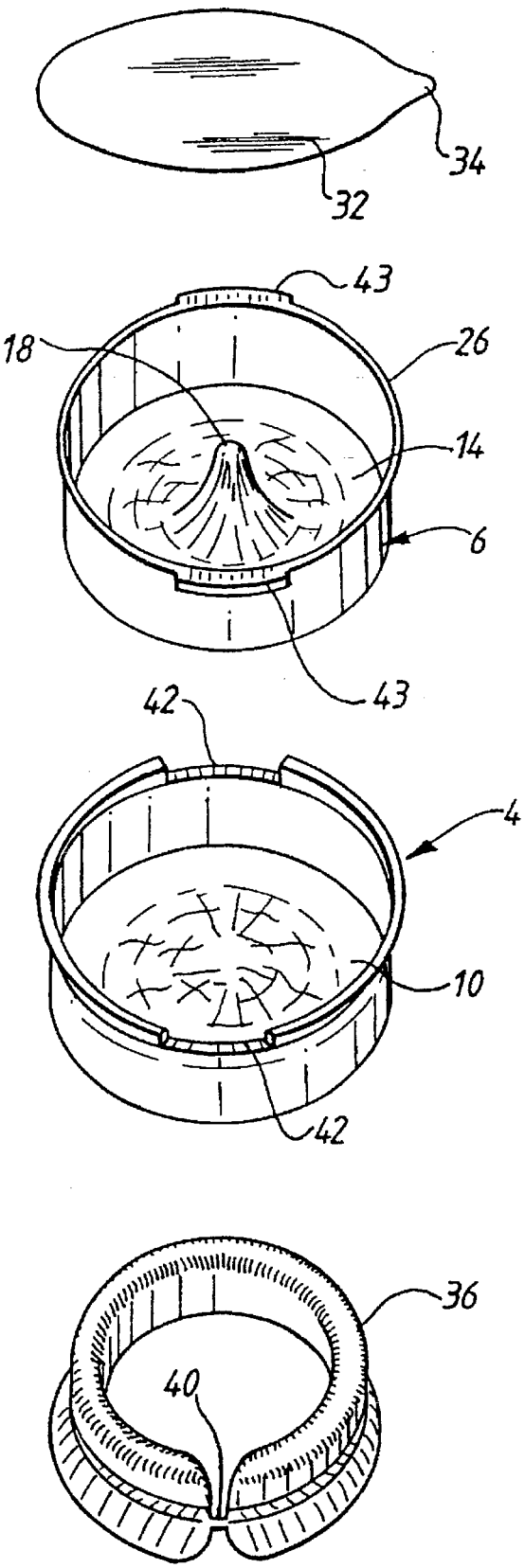
FIG. 5 is an exploded view of the packaged condom as shown in FIG. 1.
Figure 6:
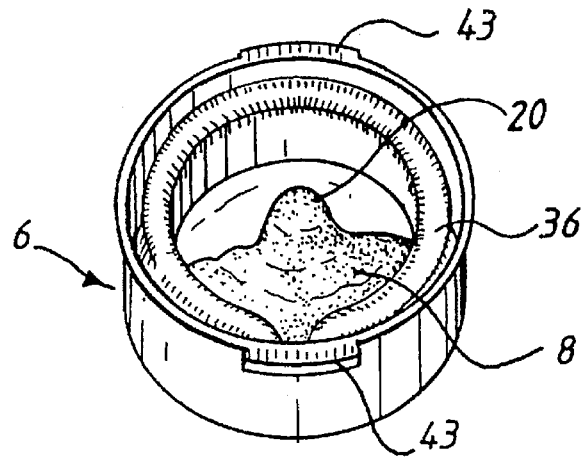
FIG. 6 is a perspective view of the first container and its contents.
Figure 7:
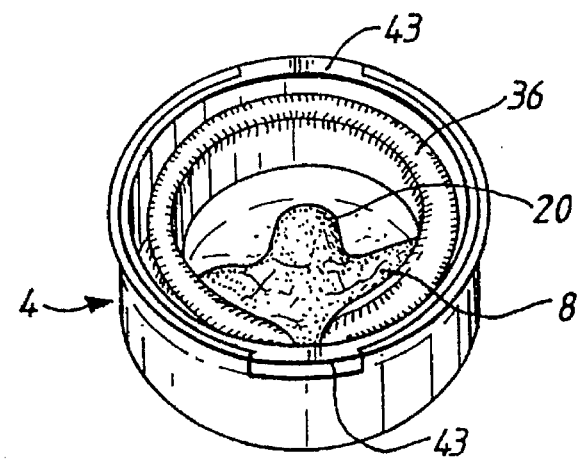
FIG. 7 is a perspective view of the packaged condom as shown in FIG. 1 but without a foil seal.

The first and the second containers 4, 6 are sealed by an aluminium metallised plastics laminate foil seal 32. As shown in FIG. 5, the foil seal 32 has a pull portion 34 for enabling the foil seal 32 to be opened. The foil seal 32 extends over the edge of the second container 6 and also over the edge of the first container 4 as can be seen from FIG. 1. Thus the foil seal 32, which is heat sealed in position, seals the second container 6 in the first container 4.

As can be seen from FIG. 1, the closed end portion 20 of the condom 8 is in the form of a teat.

As can be seen from FIGS. 1, 3 and 5–7, the packaged condom 2 includes an applicator in the form of a ring 36 for applying the condom 8. The ring 36 has a grooved portion 38 for holding the condom 8 as shown in FIGS. 1 and 3. As shown in FIG. 3, the ring 36 has a frangible joint 40 which is adapted to be broken during use of the ring 36 in applying the condom 8. Thus, more specifically, when the ring 36 has been used to unroll the condom 8 along the length of a penis, the breaking of the frangible joint 40 enables the ring 36 to be removed from the penis whilst the condom 6 is left in position on the penis. The frangible joint 40 may be an adhesive frangible joint 40.

Figure 8:
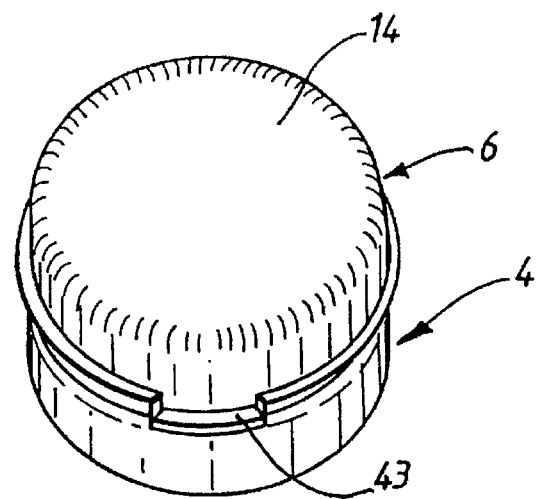
FIG. 8 is a perspective view of the packaged condom as shown in FIG. 3.

FIG. 5 illustrates how the first container 4 has two slots 42 in its periphery. These slots 42 extend for 30°. The slots 42 are to enable the second container 6 to be pushed down into the first container 4 to the position shown in FIGS. 3, 4 and 8, this position requiring lugs 43 on the lip 26 of the second container 6 to move sufficiently far into the first container 4 that the lip 26 locates in the peripheral groove 24.

The packaged condom 2 is advantageous in that the first and the second containers 4, 6 can be relatively rigid in order to protect the condom 8 before use. The first and the second containers 4, 6 can be made from plastics materials, for example by moulding. The presence of the upstanding locating member 18 ensures that a user opening the packaged condom 2 will always find the condom 8 the right way up. Still further, the upstanding locating member 18 facilitates gripping of the condom 8, for example in the case where the ring 36 is not present or where a user does not wish to use the ring 36. If the ring 36 is employed, then contact with the condom 6 can be minimised or avoided. After use of the condom 6, the packaged condom 2 provides a simple, hygienic and discreet way of storing the used condom 6 for disposal.

It is to be appreciated that the embodiment of the invention described above with reference to the accompanying drawings has been given by way of example only and that modifications may be effected. Thus, for example, the condom 8 may be a condom that does not have a closed end portion 20 in the form of a teat. Also, the ring 36 could be omitted.

I claim:

1. A packaged condom comprising a first container, a second container positioned inside the first container, and a condom sealed inside the second container: the first container comprising a base and an upstanding side wall; the second container comprising a base, an upstanding sidewall, and an upstanding locating member; the condom comprising a closed end portion which is located on the upstanding locating member; and the packaged condom being such that the first and the second containers are separable from each other such that after use of the condom the first and the second containers are connectable together to form a closed receptacle for the used condom.

2. A packaged condom according to claim 1 in which the first and the second containers are connectable together to form a closed receptacle which is not re-openable.

3. A packaged condom according to claim 2 in which the first and the second containers are connectable together to form the closed receptacle such that the second container forms a lid for the first container.

4. A packaged condom according to claim 3 in which the second container is such that it is turned upside down to form the lid for the first container.

5. A packaged condom according to claim 1 in which the side wall of the first container has an inner face with a peripheral groove in it, in which the side wall of the second container has an outwardly directed lip, and in which the lip locates in the peripheral groove when the first and the second containers are connected together to form the closed receptacle.

6. A packaged condom according to claim 5 in which the peripheral groove has an upper edge defined by a peripheral bead which acts to lock the first and the second containers together when they are connected together to form a closed receptacle.

7. A packaged condom according to claim 1 in which the second container has a foil seal for sealing the condom in the second container.

8. A packaged condom according to claim 7 in which the foil seal extends over the first container and thus seals the second container in the first container.

9. A packaged condom according to claim 1 and including an applicator for applying the condom.

10. A packaged condom according to claim 9 in which the applicator is in the form of a ring which has a grooved portion for holding the condom.

* * * * *